(12) United States Patent
Murray et al.

(10) Patent No.: US 12,102,312 B2
(45) Date of Patent: Oct. 1, 2024

(54) EXPANDABLE DEVICES, SYSTEMS, AND METHODS

(71) Applicant: BOSTON SCIENTIFIC SCIMED, INC., Maple Grove, MN (US)

(72) Inventors: Collin Murray, Bolton, MA (US); Kathryn Gildersleeve, Maple Grove, MN (US); Paul Smith, Smithfield, RI (US); Amanda Lynn Smith, Boston, MA (US); James J. Scutti, Norwell, MA (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 0 days.

(21) Appl. No.: 17/880,062

(22) Filed: Aug. 3, 2022

(65) Prior Publication Data

US 2023/0040939 A1    Feb. 9, 2023

Related U.S. Application Data

(60) Provisional application No. 63/228,700, filed on Aug. 3, 2021.

(51) Int. Cl.
*A61B 17/02*    (2006.01)
*A61B 1/32*    (2006.01)

(52) U.S. Cl.
CPC ............ *A61B 17/0218* (2013.01); *A61B 1/32* (2013.01); *A61B 2017/0225* (2013.01)

(58) Field of Classification Search
CPC .................. A61B 17/0218; A61B 1/32; A61B 2017/00269; A61B 2017/0445

USPC .................................................. 600/188–245
See application file for complete search history.

(56) References Cited

U.S. PATENT DOCUMENTS

| 6,530,934 | B1 | 3/2003 | Jacobson et al. | |
| 2001/0049509 | A1* | 12/2001 | Sekine | A61B 1/018 600/104 |
| 2004/0249367 | A1* | 12/2004 | Saadat | A61B 1/2736 600/101 |

(Continued)

OTHER PUBLICATIONS

Invitation to Pay Additional Fees dated Nov. 21, 2022 for International Application No. PCT/US2022/039265.

*Primary Examiner* — Eduardo C Robert
*Assistant Examiner* — Tara Rose E Carter
(74) *Attorney, Agent, or Firm* — Seager, Tufte & Wickhem, LLP

(57) ABSTRACT

This disclosure relates to the field of luminal surgery. Specifically, the present disclosure relates to medical devices that expand within a body lumen for accessing a target tissue. In an aspect, an expandable device for a body lumen may include a filament comprising a proximal end, a distal end, and a length. The device may include a plurality of segments. Each segment may comprise a middle portion comprising a longitudinal axis extending axially therethrough, a projection portion extending from an end of the middle portion along the longitudinal axis, and a receptive portion extending from an opposing end of the middle portion away from the longitudinal axis, the receptive portion configured to receive the projection portion of an adjacent one of the plurality of segments. An aperture may be disposed through the projection portion, the middle portion, and the receptive portion.

20 Claims, 7 Drawing Sheets

(56) References Cited

U.S. PATENT DOCUMENTS

| | | | |
|---|---|---|---|
| 2009/0149716 A1* | 6/2009 | Diao | A61B 17/0218 |
| | | | 600/207 |
| 2015/0142044 A1 | 5/2015 | Schwab et al. | |
| 2016/0278757 A1* | 9/2016 | Piskun | A61B 1/313 |
| 2019/0328424 A1 | 10/2019 | Suddaby | |
| 2020/0054472 A1 | 2/2020 | Miesse et al. | |

* cited by examiner

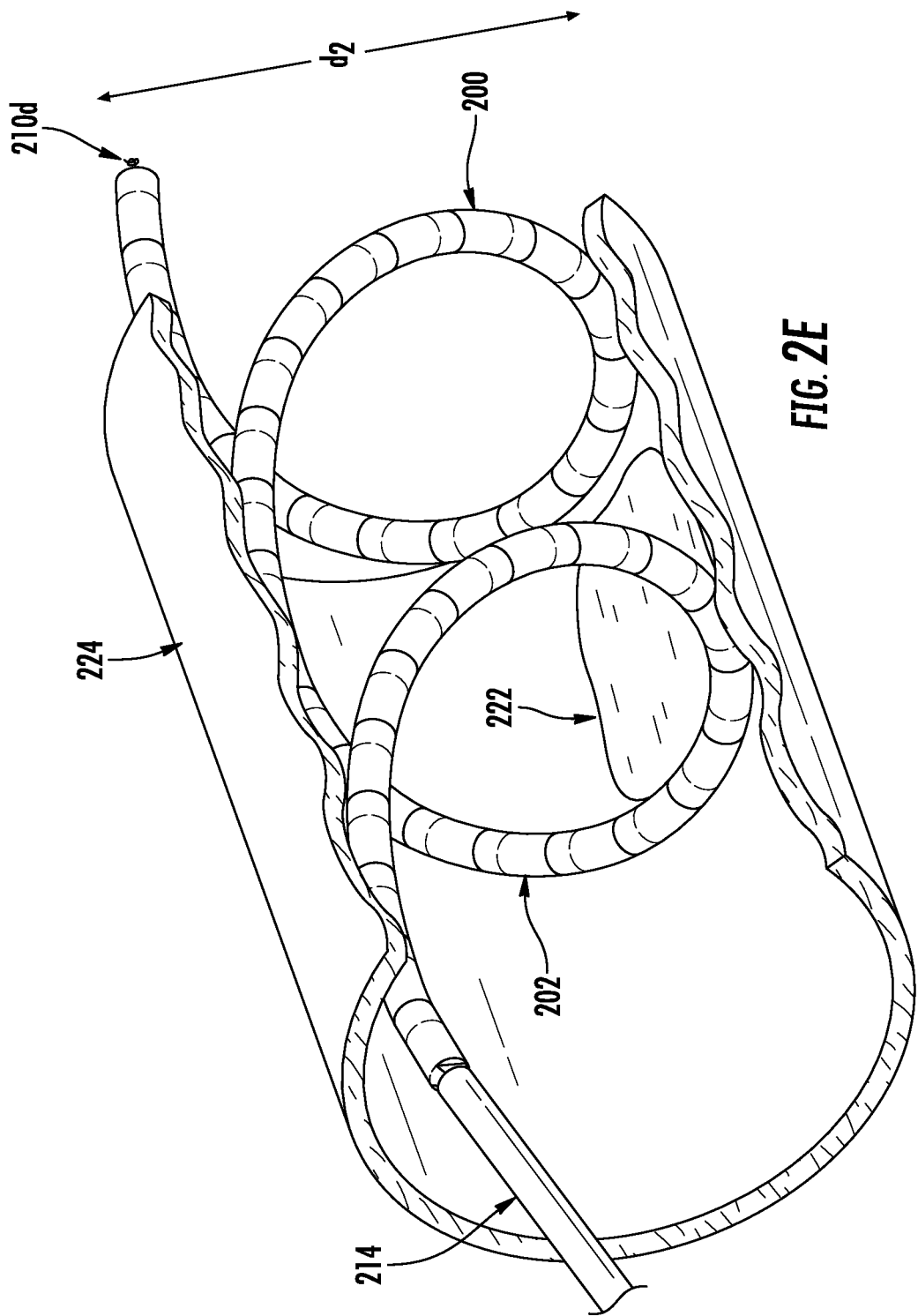

EXPANDABLE DEVICES, SYSTEMS, AND METHODS

CROSS-REFERENCE TO RELATED APPLICATIONS

This application claims the benefit of priority of U.S. Provisional Application No. 63/228,700, filed Aug. 3, 2021, the entire disclosure of which is hereby incorporated by reference herein for all purposes.

FIELD

This disclosure relates to the field of luminal surgery. Specifically, the present disclosure relates to medical devices that are expandable within a body lumen for accessing a target tissue, e.g., during a dissection procedure.

BACKGROUND

Surgical dissection of lesions from within narrow body passages, such as the digestive tract, may be inefficient and time-consuming due to poor target tissue visualization during the dissection procedure. This problem may be exacerbated during the procedure as the surrounding tissue of a body lumen and/or as the partially dissected target tissue often obstructs the working area to further decrease visibility and obstruct medical tools. It is with these considerations that the expandable devices, systems, and methods of this disclosure may be useful.

SUMMARY

This disclosure, in its various aspects, is directed generally to expandable devices, systems, and methods within a body lumen increasing access and/or visibility of a target tissue and/or decreasing complications, procedure time, and/or complexity. In an aspect described within the scope of the disclosure, an expandable device for a body lumen may include a filament comprising a proximal end, a distal end, and a length. The device may include a plurality of segments. Each segment may comprise a middle portion comprising a longitudinal axis extending axially therethrough, a projection portion extending from an end of the middle portion along the longitudinal axis, and a receptive portion extending from an opposing end of the middle portion, the receptive portion extending in a direction away from the longitudinal axis, the receptive portion configured to receive the projection portion of an adjacent one of the plurality of segments. An aperture may be disposed through the projection portion, the middle portion, and the receptive portion. The filament may extend through the aperture of each segment. The device may comprise a delivery configuration having a first outer dimension and a tensioned configuration having a second outer dimension larger than the first outer dimension.

In various embodiments, the plurality of segments may abut adjacent segments of the plurality of segments along the filament to form an expanded shape in the tensioned configuration. The tensioned configuration may be achieved by proximally translating the filament with respect to a stop member disposed about the filament to thereby press each of the plurality of segments against adjacent ones of the plurality of segments. The expanded shape may comprise a helix having a first space between first and second windings and a second space between third and fourth windings larger than the first portion. The projection portion may taper away from the middle portion to a tip having a smaller dimension than a dimension of the middle portion. The receptive portion may comprise a cavity defining a volume that compliments a shape of the projection portion. Each of the plurality of segments may comprise a ridge configured to engage an adjacent one of the plurality of segments. The tip of the projection portion may terminate at a first axis transverse with a centerline extending through the segment. The projection portion may be symmetrical across the first axis. The cavity of the receptive portion may terminate at a second axis transverse with the centerline. The receptive portion may be symmetrical across the second axis. The first axis may be angled obliquely apart from the second axis. The tip of the projection portion may comprise a first planar surface transverse with the longitudinal axis. The tip of the projection portion may terminate at a first planar surface transverse with a centerline extending through the segment. The cavity of the receptive portion may terminate at a second planar surface transverse with the centerline. A first axis may extend along the first planar surface at the largest dimension of the first planar surface. A second axis may extend along the second planar surface at the largest dimension of the second planar surface. The second axis may be angled obliquely apart from the first axis. The tip of the projection portion may comprise a first planar surface transverse with the longitudinal axis. A remainder of the projection portion may comprise two slanted planes disposed 180 degrees apart when viewed along the longitudinal axis. A remainder of the projection portion may comprise two convex surfaces may be disposed 180 degrees apart when viewed along the longitudinal axis. A remainder of the projection portion may extend from the middle portion to the tip. A perimeter of the remainder of the projection portion may comprise two slanted planes interspaced by two convex surfaces. An end portion may be disposed at the distal end of the filament. The end portion may comprise a larger dimension than a dimension of the aperture of each of the plurality of segments. The filament may engage at least one element in the tensioned configuration. The distal end of the filament may be adhered to a distal-most segment of the plurality of segments. The device may comprise an arc shape in the tensioned configuration. A suture may be coupled to an aperture of the plurality of segments. The first outer dimension may be at most about 4.2 mm. The second outer dimension may be at least 18 mm.

In an aspect, an expandable system for a body lumen may include a tubular base comprising a lumen and a longitudinal axis. A plurality of self-expanding leaves may extend from the tubular base. Each of the plurality of self-expanding leaves may have proximal and distal ends. The proximal ends may be associated with the tubular base. The plurality of self-expanding leaves may be oriented substantially parallel with the longitudinal axis in a delivery configuration. The distal ends of the plurality of self-expanding leaves may extend radially away from the longitudinal axis of the tubular base in a deployed configuration. A sheath may be slidably extended about the tubular base and the plurality of self-expanding leaves to move the plurality of self-expanding leaves between the delivery configuration and the deployed configuration.

In various embodiments, the distal end of each of the plurality of self-expanding leaves may be configured to curl outwardly away from the lumen in the deployed configuration. Each of the plurality of self-expanding leaves may comprise an end configured to curl toward a proximal end of the longitudinal axis in the deployed configuration. The distal end of each of the at least one of the plurality of self-expanding leaves may comprise an aperture configured to receive a suture. The suture may have a tissue-engaging portion for engaging tissue and for applying tension to the tissue via the associated self-expanding leaf. A catheter may extend through the lumen.

In various embodiments described herein, a method for forming a scaffold within a body lumen may include delivering a plurality of segments disposed along a filament to a working volume of the body lumen. The plurality of segments may have a delivery configuration. The filament may be proximally translated with respect to the plurality of segments to cause each of the plurality of segments to abut an adjacent other one of the plurality of segments to form a tensioned configuration having an outer dimension that is larger than an outer dimension of the delivery configuration. The plurality of segments may be maintained in the tensioned configuration by tension in the filament caused by the proximal translation.

An open space between the plurality of segments in the tensioned configuration may be aligned towards a working volume of the body lumen. Proximally translating the filament may include translating the filament with respect to a stop member disposed about the filament proximal to the plurality of segments. The tension of the filament may be released such that the plurality of segments transitions from the tensioned configuration to the delivery configuration. A first end of a tissue traction device may be coupled to a segment of the plurality of segments. A second end of the tissue traction device may be coupled to a target tissue, thereby applying tension to the target tissue.

In various embodiments described herein, a method for forming a scaffold within a body lumen may include delivering a device comprising a tubular base having a plurality of self-expanding leaves extending from the tubular base to a working volume of the body lumen. The device may have a delivery configuration with the plurality of self-expanding leaves oriented substantially parallel with a longitudinal axis of the device. A sheath disposed about the device may be proximally translated to transition the device from the delivery configuration to a deployed configuration wherein a distal end of each of the plurality of self-expanding leaves extends radially away from the longitudinal axis.

A suture coupled to a leaf of the plurality of leaves may be extended to a target tissue to apply tension to the target tissue. The device may be deployed into the body lumen from about an endoscope. The device may be retrieved by extending an endoscope through the lumen of the device and extending the sheath about the plurality of leaves thereby transitioning the device from the deployed configuration to the delivery configuration.

BRIEF DESCRIPTION OF THE DRAWINGS

Non-limiting examples of the present disclosure are described by way of example with reference to the accompanying figures, which are schematic and not intended to be drawn to scale. In the figures, each identical or nearly identical component illustrated is typically represented by a single numeral. For purposes of clarity, not every component is labeled in every figure, nor is every component of each embodiment of the disclosure shown where illustration is not necessary to allow those of skill in the art to understand the disclosure. In the figures:

FIG. 2E is an illustration of the expandable device of FIGS. 2C and 2D within a body lumen in the tensioned configuration.

DETAILED DESCRIPTION

Figure 1A:
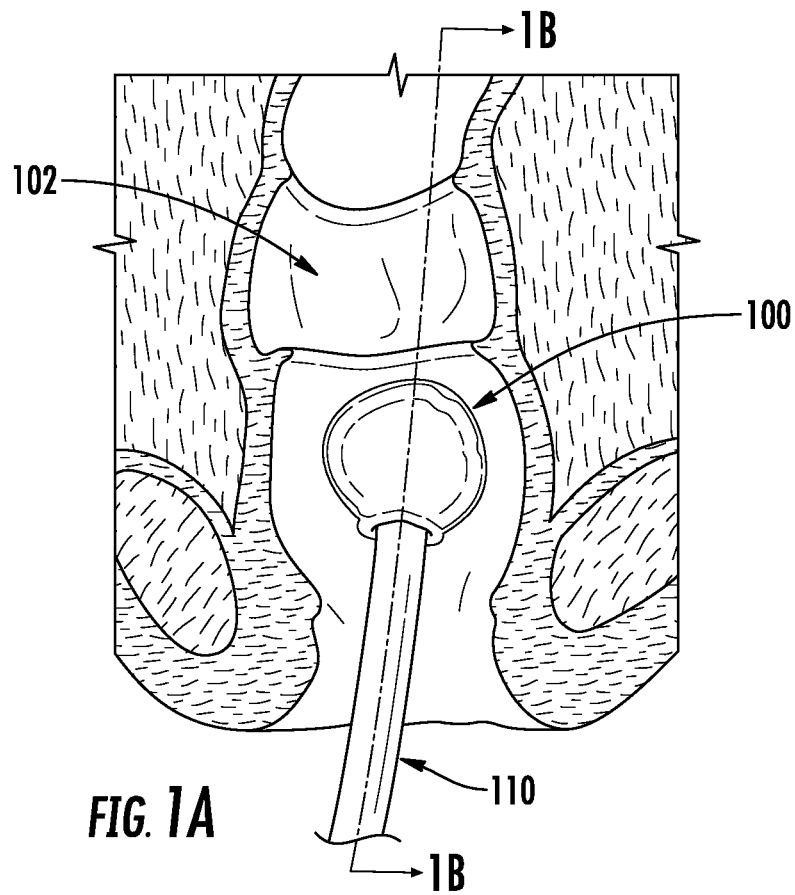
FIG. 1A is an illustration of a digestive tract body lumen including a target tissue for dissection with an endoscope according to an embodiment of the present disclosure.

The detailed description should be read with reference to the drawings, which are not necessarily to scale, depict illustrative embodiments, and are not intended to limit the scope of the invention.

As used herein, "proximal end" refers to the end of a device that lies closest to the medical professional along the device when introducing the device into a patient, and "distal end" refers to the end of a device or object that lies furthest from the medical professional along the device during implantation, positioning, or delivery.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used in connection with other embodiments whether or not explicitly described unless clearly stated to the contrary.

All numeric values are herein assumed to be modified by the term "about," whether or not explicitly indicated. The term "about", in the context of numeric values, generally refers to a range of numbers that one of skill in the art would consider equivalent to the recited value (i.e., having the same function or result). In many instances, the term "about" may include numbers that are rounded to the nearest significant figure. Other uses of the term "about" (i.e., in a context other than numeric values) may be assumed to have their ordinary and customary definition(s), as understood from and consistent with the context of the specification, unless otherwise specified. The recitation of numerical ranges by endpoints includes all numbers within that range, including the endpoints (e.g., 1 to 5 includes 1, 1.5, 2, 2.75, 3, 3.80, 4, and 5).

As used herein, the term "tissue retraction" or "retraction," refers to the ability to control the position of a tissue during a dissection procedure. For example, "retraction" may allow the dissected portion of a target tissue to be immobilized and lifted away from the dissecting plane to improve visualization of the remaining (i.e., non-dissected) target tissue, while also applying tension to the target tissue for more precise manipulation of the dissecting element.

As used herein, the term "target tissue" refers to an unhealthy, diseased (i.e., cancerous, pre-cancerous, etc.) or otherwise undesirable portion of tissue that may be healthy or unhealthy. A "target tissue" may also include tissues that are suspected of being unhealthy or diseased, but which require surgical removal for verification of their disease status by biopsy. It should be appreciated that surgical dissection of a "target tissue" typically includes removal of a portion of the surrounding healthy tissue along the "target tissue" margin to ensure complete removal and minimize the potential for metastasis of left behind or dislodged "target tissue" cells to other body locations.

A number of medical procedures, including, for example along the digestive tract, utilize medical devices to access tissue intended for manipulation, clamping, dissection, and/or resection (e.g., "target tissue") within the body. For example, in some current medical procedures (e.g., endoscopic submucosal dissection (ESD), endoscopic mucosal resection (EMR), Peroral Endoscopic Myotomy (POEM), cholecystectomy, Video-Assisted Thoracoscopic Surgery (VATS)), physicians may utilize an endoscope or similar medical device to access and remove diseased lesions. Further, as part of such procedures, a physician may utilize a catheter, such as an endoscope, capable of both accessing the layer of target tissue site while also permitting a dissecting/resecting device or clamping device to be deployed therethrough the catheter to the layer of target tissue. Additionally, in some instances, an endoscope may incorporate features which assist the physician in visualizing and performing the tissue procedure. For example, some endoscopes may include a light and/or camera designed to illuminate and/or visualize the body lumen as the endoscope is navigated and positioned adjacent to the layer of target tissue site. Additionally, some endoscopes may also include a lumen (e.g., a working channel, that may have, e.g., a diameter of about 2.8 mm, about 4.2 mm, or the like) through which a dissecting/resecting device, grasping member, delivery catheter for the same, or other accessory devices, may be deployed and utilized. Additional visualization methods may be alternatively or additionally employed, e.g., fluoroscopy.

While physicians are becoming more proficient at removing diseased lesions from within the body (e.g., within the digestive tract, abdominal cavity, thoracic cavity, etc.), present tissue tensioning methods may continue to be inefficient to the physician. For example, in some instances, poor visualization and poor ability to engage and manipulate tissue may undesirably prolong a procedure. For example, an aspect of EMR/ESD that may be difficult is the positioning and maneuvering (e.g., tensioning) of the layer of target tissue. In some EMR/ESD procedures, physicians may use separate devices to provide traction to tissue and/or patency to a body lumen of the target tissue. Such procedures may include multiple device exchanges which may extend procedure times. The use of separate devices may also result in the practitioner being unable to maintain traction, patency, or tension, applied to the layer of target tissue and/or the body lumen of the target tissue. It may also cause the practitioner to maintain or adjust tension applied to the layer of target tissue in an inefficient or inconsistent manner.

Figure 1B:
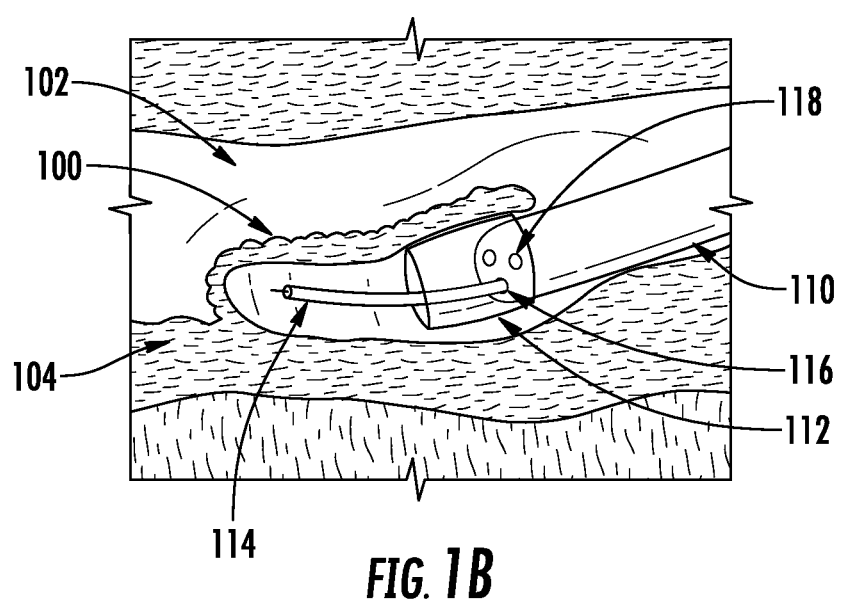
FIG. 1B is an illustration of a cross-section of FIG. 1A taken along line 1B-1B of FIG. 1A.

In various luminal procedures, a target tissue may need to be accessed by medical tools. For example, with reference to FIGS. 1A and 1B, an endoscope 110 accessing a target tissue 100 within a body lumen 102 for ESD is illustrated according to an embodiment of the disclosure. The endoscope 110 is inserted into the gastrointestinal tract body lumen 102 toward the target tissue 100. A cutting tool 114 is extended from a working channel 116 of the endoscope 110. The endoscope 110 includes a clear cap 112 to allow for a substantially unobstructed and clear view of the working area distal of the endoscope 110 for manipulating the target tissue 100 and operating the cutting tool 114 via the lens 118. With the cap 112 and endoscope 110 extended under the target tissue 100, the cutting tool 114 may be operated to dissect the target tissue 100 from surrounding tissue 104 by cutting about the perimeter of the target tissue 100. Endoscope 110 and/or cutting tool 114 access to the target tissue 100 may be impeded by complications such as the target tissue 100 folding, the surrounding tissue 104 folding, lack of body lumen 102 patency, loss of or unestablished control of the target tissue 100 during dissection, and/or operator disorientation caused by poor visibility. Expandable devices, systems, and methods described herein may assist with such complications and may be used in association with such ESD procedures.

Figure 2A:
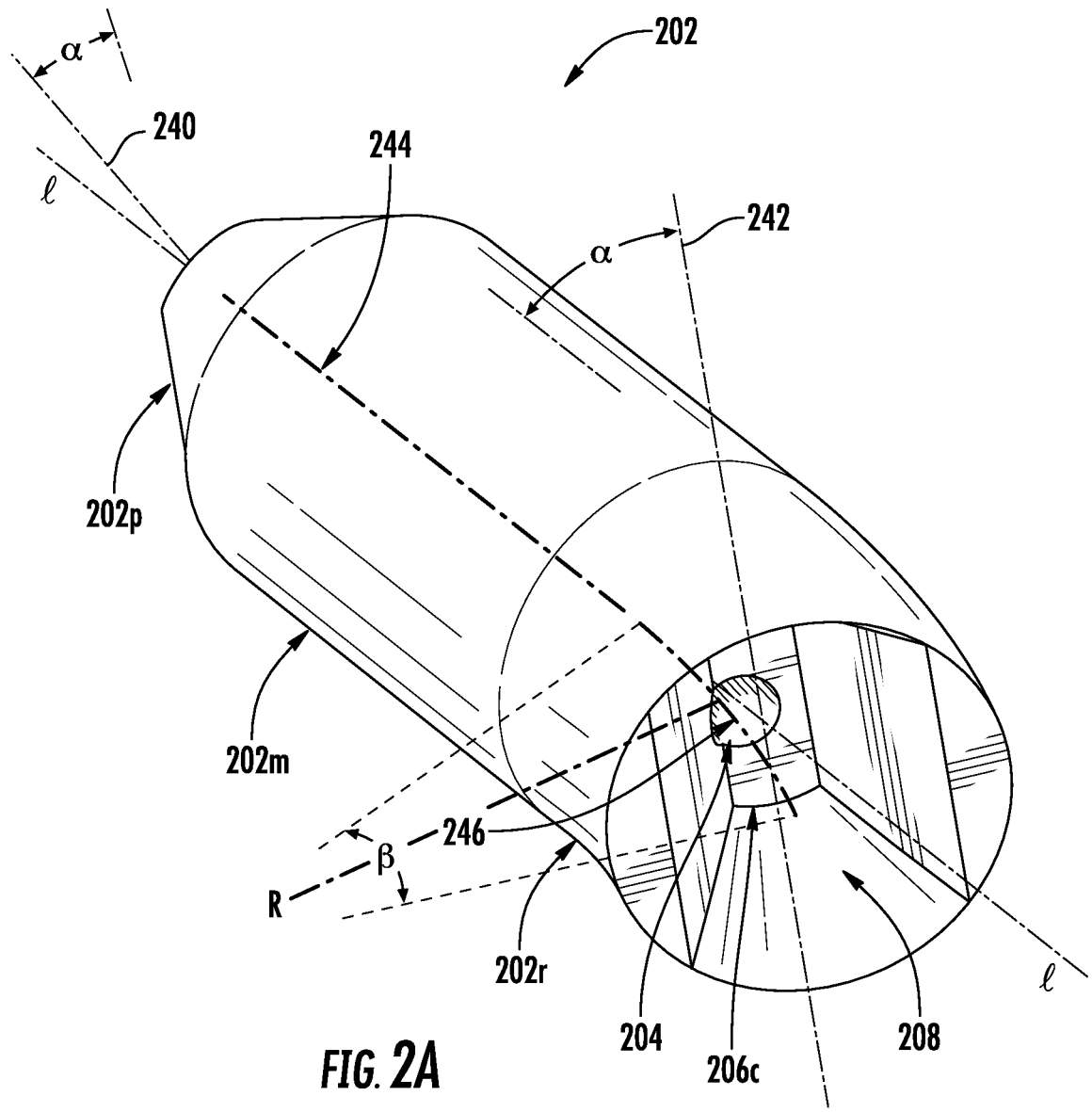
FIG. 2A is an illustration of a perspective view of a segment of an expandable device according to an embodiment of the present disclosure.
Figure 2B:
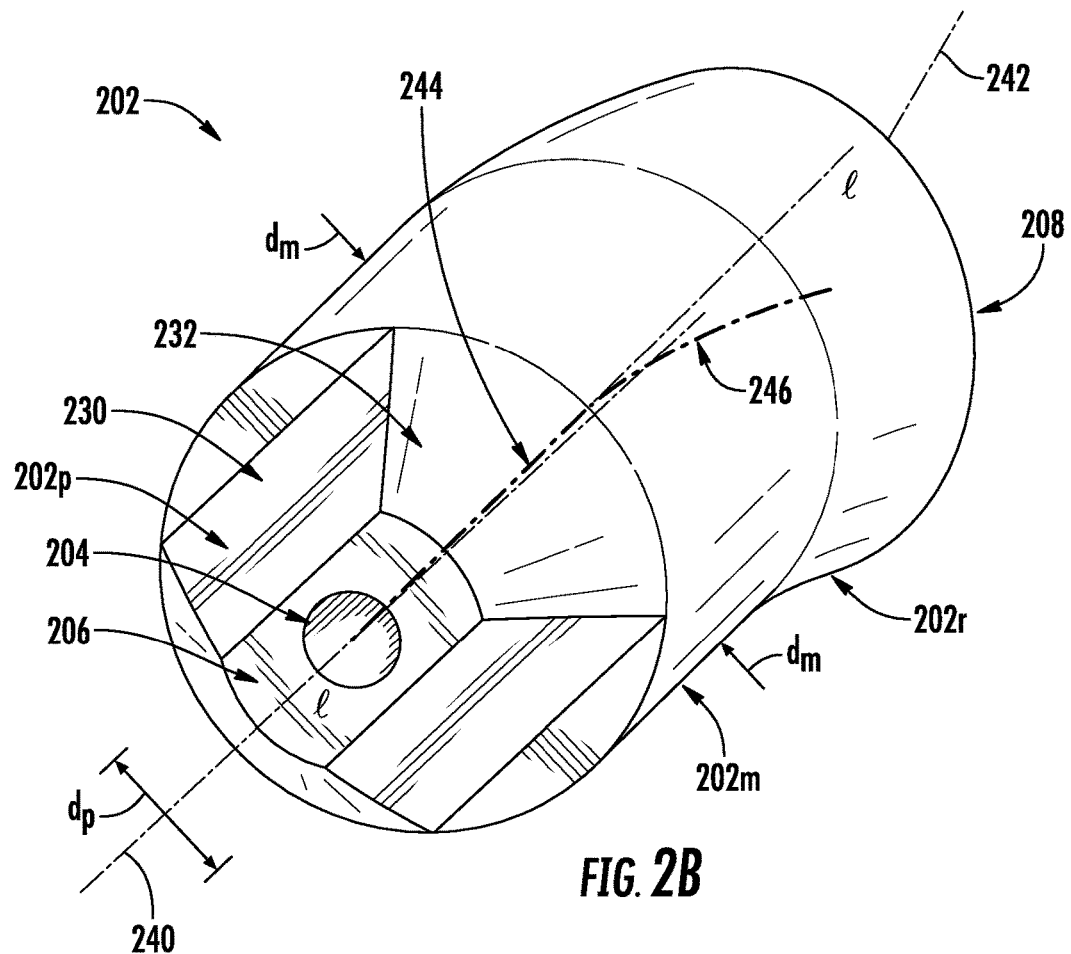
FIG. 2B is another perspective view of the segment of FIG. 2A.

With reference to FIGS. 2A and 2B, perspective views of a segment 202 for an expandable device is illustrated according to an embodiment of the present disclosure. The segment 202 includes a projection portion 202$p$ at a first end, a receptive portion 202$r$ at a second end, and a middle portion 202$m$ disposed between the projection portion and the receptive portion. The middle portion 202$m$ may have a longitudinal axis $\ell$ extending therethrough. The projection portion 202$p$ tapers from the middle portion to a tip 206 having a smaller dimension $d_p$ than a dimension $d_m$ of the middle portion 202$m$. The tip 206 of the projection portion 202$p$ can have a planar surface 206 oriented transverse to the longitudinal axis $\ell$. A first axis 244 extends along the planar surface 206 at the largest dimension of the planar surface 206. The projection portion 202$p$ may include two slanted planar portions 230 disposed between the tip 206 and the middle portion 202$m$. The slanted planar portions 230 can each form an oblique angle with respect to the longitudinal axis $\ell$. In the illustrated embodiment these planar portions 230 are disposed 180-degrees apart when viewed along the longitudinal axis $\ell$. A pair of convex surfaces 232 may be disposed between the slanted planar portions 230.

The receptive portion 202$r$ extends away from the middle portion 202$m$ along a curved portion 246 of a centerline 244 of the segment 202. As can be seen, the centerline 244 of the segment 202 is a line extending through the center of the segment 202 that is coincident with the longitudinal axis $\ell$ along the middle portion 202 and the projection portion 202$p$, but which curves away from the longitudinal axis $\ell$ at the receptive portion 202$r$. The curved portion 246 of the centerline 244 extends away from the longitudinal axis $\ell$ having a radius of curvature $\beta$ at a radius R. The radius of curvature $\beta$ and the radius R may depend on available working channel dimensions during delivery, working area dimensions, and/or a desired size or number of rotations per length of the device when deployed. The receptive portion 202r includes a cavity 208 defining a recess having a shape that compliments the shape of the projection portion 202p. A depth of the cavity 208 of the receptive portion 202r terminates at a planar surface 206c that compliments the tip 206 of an adjacent segment 202. A second axis 242 extends along the planar surface 206c at the largest dimension of the planar surface 206c. The second axis 242 and the planar surface 206c are transverse to the curved portion 246 of the centerline 244. The cavity 208 is further defined by two slanted planes 230c interspaced by two convex surfaces 232c that are complimentary to the slanted planes 230 and convex surfaces 232 of the projection portion 202p of an adjacent segment 202. The first axis 240 is angled obliquely with respect to the second axis 242 at an angle α. Thus arranged, the receptive portion 202r is configured to receive the projection portion 202p of an adjacent segment 202 as will be described in relation to FIGS. 2C-2E. The segment 202 may also include an aperture 204 through the segment 202 that may accept a filament that links multiple segments 202 together as will be described in greater detail.

Figure 2C:
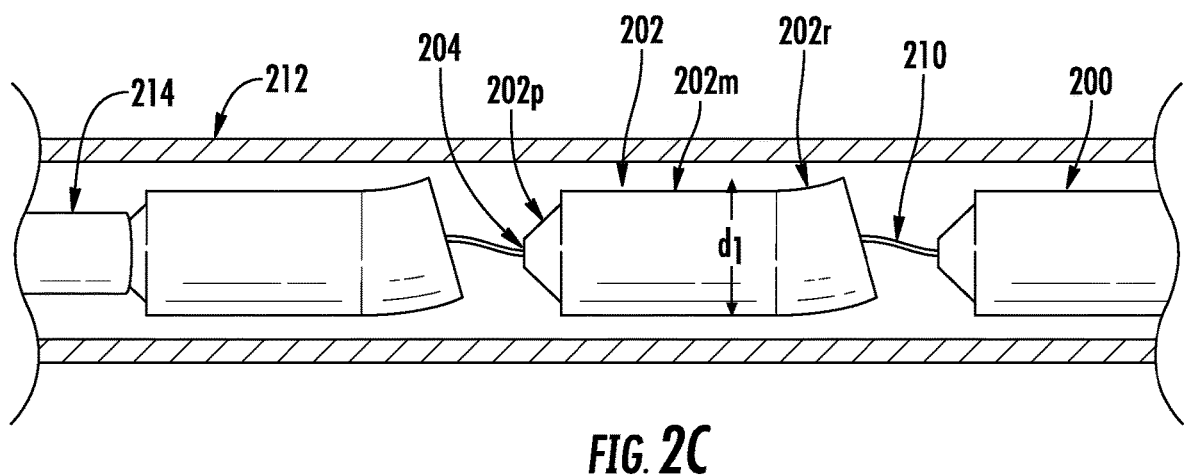
FIG. 2C is an illustration of a system including an expandable device having multiple segments of FIGS. 2A and 2B in a delivery configuration according to an embodiment of the present disclosure.

Referring to FIG. 2C, a system including an expandable device 200 having multiple segments 202 of FIGS. 2A and 2B is illustrated according to an embodiment of the present disclosure. As illustrated, the segments 202 are oriented so that a projection portion 202p of one segment 202 is positioned adjacent to a receptive portion 202r of an adjacent segment 202. A filament 210 extends through the aperture 204 of each segment 202 such that all the segments 202 can be loosely coupled during delivery of the device 200. Although three segments 202 are illustrated, FIG. 2C only illustrates a portion of the device 200 and it will be appreciated that a greater number of segments 202 can be used. In various embodiments herein, any number of segments 202 may be used, e.g., 2, 4, 5, 8, 10, 15, 20, 30, 50, 75, 100, 200, or the like.

Still referring to FIG. 2C, the device 200 is illustrated in a delivery configuration. In the delivery configuration, the segments 202 may not be fixedly engaged with each other (although contact between segments 202 is possible in the delivery configuration). The device 200 has a first outer dimension $d_1$ (e.g., a diameter, a width, a thickness, or the like) in the delivery configuration. In one non-limiting example embodiment the device 200 may be disposed within a sheath 212 for delivery within a patient such that the device 200 may be controlled during delivery and such that the device 200 does not make contact with a working channel or patient anatomy during delivery. Once the device 200 has been positioned at a targeted location within the patient, the device 200 may be deployed from within the sheath 212 toward a target tissue by moving the sheath 212 proximally with respect to a stop member 214 that is located proximal to the device 200 (e.g., proximally retracting the sheath 212 and/or distally translating the stop member 214). The device 200 may remain in the delivery configuration once deployed from the sheath 212, and the filament 210 and one or more of the segments 202 may not remain substantially parallel with the sheath 212 (e.g., the filament 210 may curl or bend and/or the segments 202 may move/rotate or contact each other in the delivery configuration). The sheath 212 may maintain orientation and/or alignment of the segments 202 such that when the sheath 212 is retracted as or before the filament is partially or fully proximally translated, the segments 202 engage each other at a desired orientation.

Figure 2D:
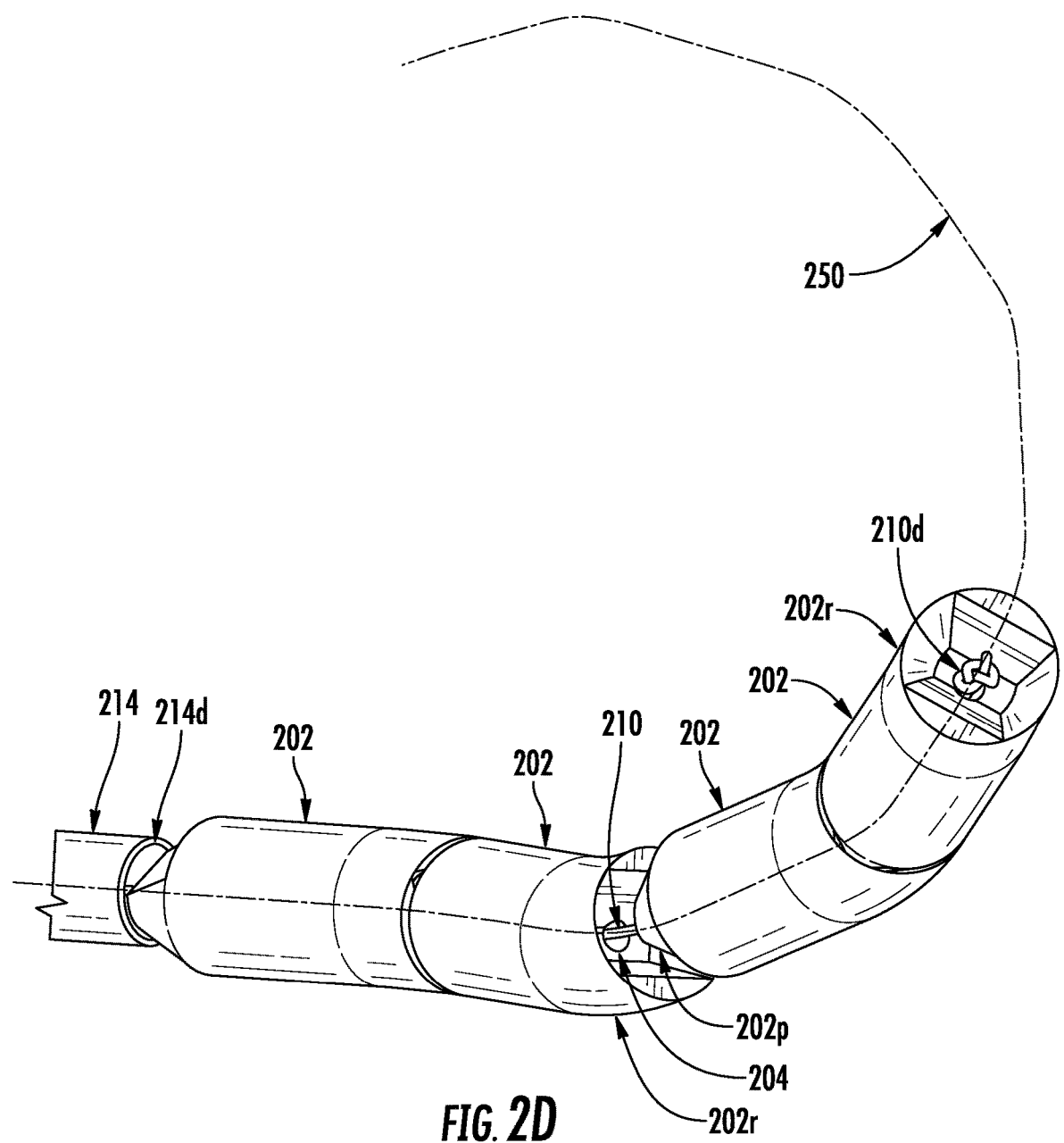
FIG. 2D is an illustration of the expandable device of FIG. 2C in a partially exploded and tensioned configuration.

With reference to FIG. 2D, the device 200 of FIG. 2C is illustrated in a tensioned configuration. To achieve the tensioned configuration, the filament 210 may be pulled proximally such that a distal end 210d of the filament 210, which may have a larger dimension than a dimension of the aperture 204 of the distal-most segment, is translated proximally into contact with the receptive portion 202r of the distal-most segment 202. Because the distal end 210d of the filament 210 has a larger dimension than that of the aperture 204 of the distal-most segment, the filament 210 engages the receptive portion 202r and pulls the associated segment 202 towards the other segments 202 of the device 200, thereby bringing the segments 202 into contact with each other. As adjacent segments 202 contact each other, a projection portion 202p of one segment 202 engages a receptive portion 202r of the adjacent segment 202. Further proximal translation of the filament 210 will press each segment 202 of the device 200 into abutment with adjacent segments 202. As the segments 202 are drawn together via proximal translation of the filament 210, a proximal-most segment 202 may engage a distal end 214d of a stop member 214 (e.g., a tubular member, a catheter, an endoscope, or the like). As the distal end 210d of the filament 210 moves towards the stop member 214 (i.e., with one or both of the distal end 210d of the filament 210 and the distal end 214d of the stop member 214 moving towards each other) the distal end 214d of the stop member 214 prevents further proximal translation of the segments 202. The segments 202 cannot translate more proximally than the distal end 214d, and thus further proximal translation of the filament 210 applies tension to the device 200 such that adjacent segments 202 engage each other.

As adjacent segments 202 engage each other, the shapes and orientations of the projection portions 202p and the receptive portions 202r cause the device 200 to assume a predetermined shape in the fully tensioned configuration. As previously described in relation to FIGS. 2A and 2B, the projection portion 202p includes a tapering tip 206 that may gradually engage, align with, and/or "key" into a complimentary receptive portion 202r of an adjacent segment 202. In the illustrated embodiment, projection portions 202p engage receptive portions 202r of adjacent segments 202 in the tensioned configuration to cause the device 200 to assume a helical shape with a helical device centerline 250. This arrangement of adjacent segments 202 occurs in the tensioned configuration because each receptive portion 202r extends along the curved portion 246 of the centerline 244 (as illustrated in FIGS. 2A and 2B) and because the axes 240, 242 of the portions 202p, 202r are angled with respect to each other (also as illustrated in FIGS. 2A and 2B) thereby turning each adjacent segment 202 along the helical centerline 250. Because each segment 202 includes a β angled receptive portion 202r in addition to the α angled axes 240, 242 of the projection portion 202p and the receptive portion 202r, respectively, the tensioned shape of the device 200 forms a helix (i.e., rather than forming a two-dimensional arc in a single plane, the tensioned shape extends in a third dimension forming a helix). The orientations of the projection portion 202p and the receptive portion 202r of along each segment 202 determines the overall shape of the device as the segments 202 engage each other.

Referring to FIG. 2E, the device 200 of FIGS. 2C and 2D is illustrated in the tensioned configuration within a body lumen 220. As can be seen, in the tensioned configuration the device 200 is an expanded helical shape that expands and/or otherwise supports the body lumen 220. With tension maintained, the segments 202 engage adjacent segments 202 to form the expanded helical shape having a second outer dimension $d_2$ larger than the first outer dimension $d_1$ of the device 200 in the delivery configuration as illustrated in FIG. 2C. In the tensioned configuration of the device 200 illustrated in FIG. 2E, the device 200 contacts the surrounding tissue 224 to generally establish patency and stabilization in the body lumen 224 and create a scaffolding about a working area to enable access to a target tissue 222. Expansion of the device 200 occurs independently from the sheath 212 or an endoscope such that the sheath 212 or endoscope may be manipulated for the procedure as desired without affecting the scaffolded device 200. In some embodiments, the tensioned device 200 is oriented such that the target tissue 222 is located within a space between adjacent helical windings of the tensioned device 200. This allows for medical tools to access the target tissue 222 without interference from the device 200 structure.

In various embodiments herein, a device 200 may form a helix in which a first portion of the helix has a space between windings that is greater than a space between windings of a second portion of the helix. With such embodiments, the larger space of the first portion of the helix may be positioned adjacent to the target tissue 222 to maximize an open working area about the target tissue 222. In other embodiments the distance between adjacent windings may remain constant along the length of the device 200, while the diameter d2 of the device may vary along the device 200 to achieve a desired geometry. In still further embodiments the individual segments 202 may not all be of the same shape and/or size and/or may be configured to achieve different shapes (e.g., oval, sinusoid, S-shape, zig-zag, a combination thereof, or the like).

After the target tissue 222 has been treated, tension may be released on the filament 210 such that the device 200 transitions from the tensioned configuration to the delivery configuration. In the delivery configuration, the device 200 may be proximally translated away from the target tissue 222 into a sheath or a working channel for removal from the patient, or for repositioning to a different location within the body lumen 224 where it may be expanded into the tensioned configuration again.

In various embodiments, a segment may have one or more portions of various geometry that may be different from other portions. For example, projection portions and/or receptive portions may be angled, curved, or straightened with respect to other portions or with respect to portions of the shape of the device in the tensioned configuration. Segments may include a ridge, channel, bump, protrusion, hatching, texturing, or the like configured to engage an adjacent segment and to reduce slipping between segments. One or more surfaces of a segment may be concave or convex and may be configured to engage a complimentary concave or convex surfaces of an adjacent segment.

In various embodiments, the distal end 210d of the filament 210 may have a dimension larger than a dimension of one or more apertures of a segment 202. The distal end of the filament 210 may be a knotted portion or a body may be coupled thereto. The distal end may be adhered to a segment 202, e.g., a distal-most segment of a device 200. In various embodiments, tension may be maintained in the filament 210 by holding, pinching, clamping, tying, looping, locking, or the like, of a proximal portion of the filament such that the device 200 remains in the tensioned configuration as desired during treatment of a target tissue 222. In some embodiments the proximal portion of the filament 210 may be manipulated by a user at a handle portion of the system.

Figure 3A:
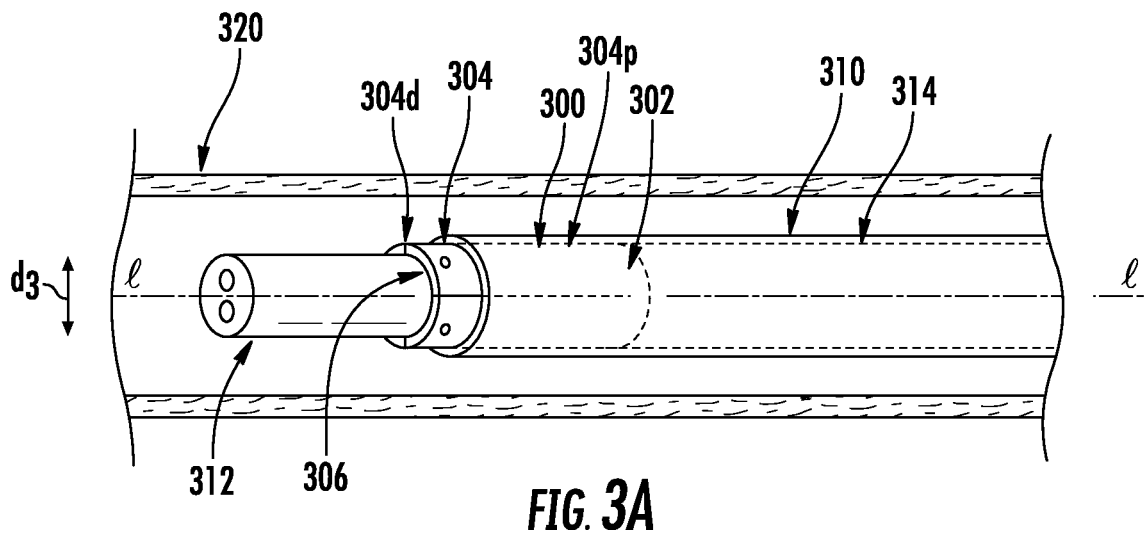
FIG. 3A is an illustration of an expandable device having a plurality of leaves in a delivery configuration within a body lumen according to an embodiment of the present disclosure.

Referring to FIG. 3A, an expandable device 300 is illustrated being delivered into a body lumen 320 according to an embodiment of the disclosure. The device 300 includes a tubular base 302 having a lumen 306 and a longitudinal axis ℓ. Four self-expanding leaves 304 extend distally from the tubular base 302. Although four leaves 304 are depicted, any number of leaves 304 may be used, e.g., 2, 3, 5, 6, 8, 10, 20, 50, etc. Each of the self-expanding leaves 304 have a distal end 304d and a proximal end 304p that is associated with the tubular base 302. The device 300 is illustrated in a delivery configuration with the leaves 304 oriented substantially parallel with the longitudinal axis ℓ. A sheath 310 is slidably disposed about the device 300, constraining the self-expanding leaves 304 in the delivery configuration. In the delivery configuration, the device 300 has a first outer dimension $d_3$. In the illustrated embodiment an endoscope 312 is slidably disposed through the lumen 306 of the device 300. The endoscope 312 may be used to navigate patient anatomy, view the working area, and assist with guiding the device 300 for deployment. A pusher 314 may be disposed within the sheath 310 and may be located proximally of the device 300 to assist with moving the device 300 about the endoscope 312 and/or within the sheath 310 for delivery and/or deployment. Although the leaves 304 are illustrated with the tips 304d oriented distally in the delivery configuration, it will be appreciated that a device 300 may instead be introduced with the tips 304d oriented proximally in the delivery configuration.

Figure 3B:
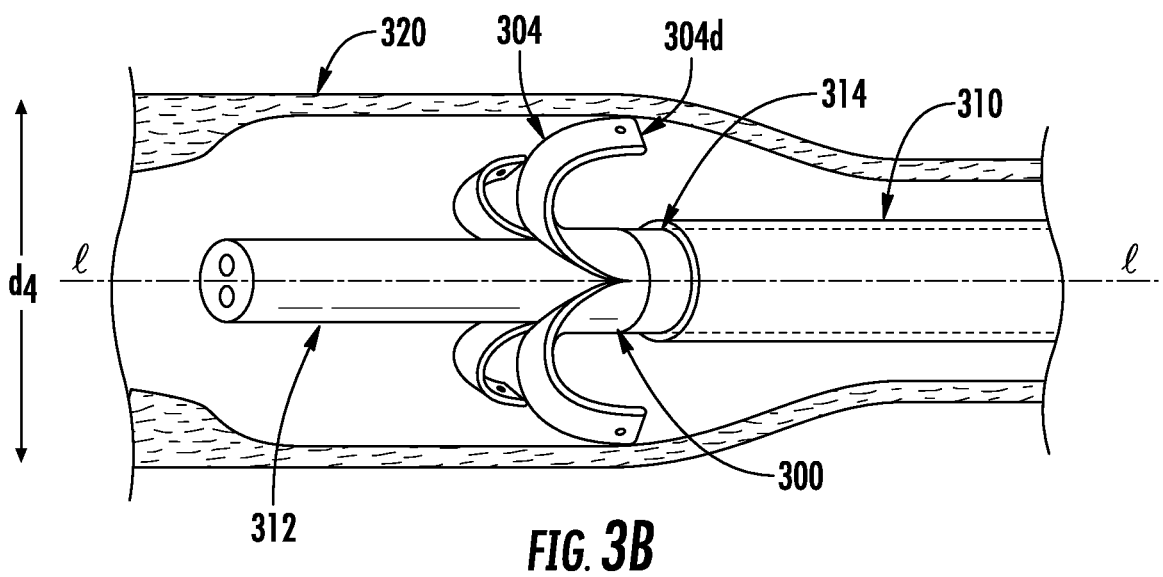
FIG. 3B is an illustration of the device of FIG. 3A in a deployed configuration.

Referring to FIG. 3B, the expandable device 300 of FIG. 3A is illustrated in a deployed configuration. To transition the device 300 to the deployed configuration the sheath 304 can be proximally retracted with respect to the pusher 314 and the self-expanding leaves 304. During this movement of the sheath 310 the pusher 314 may serve to hold the device 300 stationary such that the self-expanding leaves 304 are exposed when the sheath is retracted. Once uncovered, the distal ends 304d of the self-expanding leaves 304 may extend radially away from the longitudinal axis ℓ so that the distal ends 304d contact tissue walls of the body lumen 320 (e.g., an inside surface of the leaves 304 and/or the distal ends 304d). In the illustrated embodiment, as the leaves 304 expand to the deployed configuration, the distal ends 304d curl so that they are oriented toward a proximal end of the device. In the deployed configuration, the device 300 has a second outer dimension $d_4$ larger than the first outer $d_3$ dimension of the device in the delivery configuration. As such, in the deployed configuration the device 300 expands and/or otherwise supports the body lumen 320. In an alternative embodiment, the leaves 304 may deploy such that the distal ends 304d do not curl proximally and instead expand radially such that the distal ends 304d are oriented in a distal direction of the system.

As will be appreciated, the device 300 may be transitioned from the delivery configuration to the deployed configuration while the device remains disposed about the endoscope 312. Such an arrangement may facilitate positioning of the device 300. Alternatively, the device 300 may be deployed from the endoscope 312 by proximally retracting the endoscope 312 and/or by distally pushing the pusher 314. The device 300 may be transitioned from the fully or partially deployed configuration to the delivery configuration by extending the sheath 310 distally over the leaves 304, e.g., for retrieval or repositioning. Although a sheath 310 is illustrated, it should be understood that the device 300 could instead be sized so that it may be received within a working channel of an endoscope without the use of a separate sheath. In addition, although the device 300 is illustrated as being disposed about the endoscope 312, it should be understood that the device 300 could instead be disposed about a guidewire or catheter.

Figure 3C:
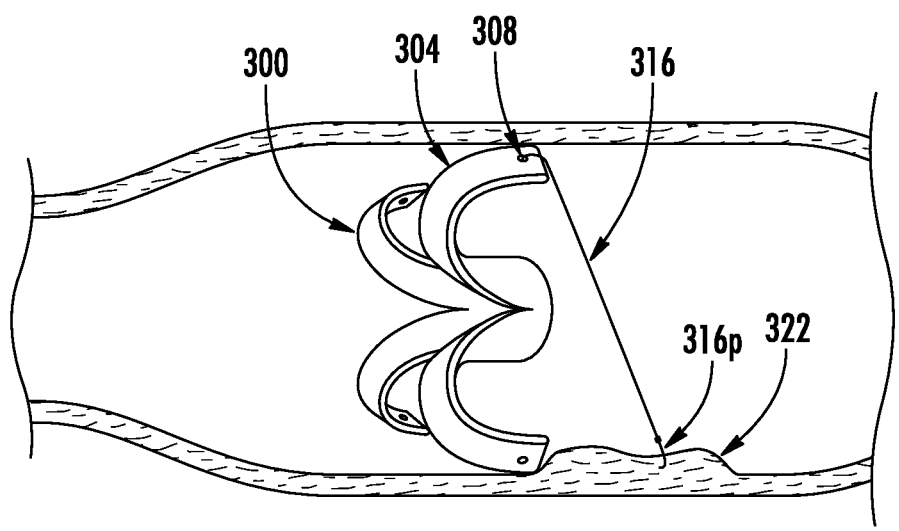
FIG. 3C is an illustration of the device of FIGS. 3A and 3B in a deployed configuration and applying tension to a target tissue It is noted that the drawings are intended to depict only typical or exemplary embodiments of the disclosure. Accordingly, the drawings should not be considered as limiting the scope of the disclosure.

Referring to FIG. 3C, the device 300 is illustrated in the deployed configuration, and separate from the endoscope 312 and sheath 310 of FIGS. 3A and 3B. In the illustrated embodiment the device 300 is expanded such that the self-expanding leaves 304 hold open the body lumen 320 at a location distal of, but proximal to, target tissue 322. The device 300 thus establishes a scaffolded working area near the target tissue 322 for treatment independent of the endoscope 312 such that the endoscope 312 may be manipulated as part of a procedure as desired. The self-expanding leaves 304 may include an aperture 308 configured to receive a suture 316 (e.g., a filament, a string, a wire, a traction device, a band, a tension member, etc.). The suture 316 may be attached to the aperture 308 after deployment of the device 300, or the suture 316 may be pre-attached to the device 300. The suture 316 may include a tissue-engaging portion 316p for engaging the target tissue 322 via, e.g., a hook, a clamp, a clip, a sharp point, or the like. The tissue-engaging portion 316p may engage the target tissue so that tension may be applied between the aperture 308 and the target tissue 322. This tension may enable the user to manipulate the target tissue 322 to facilitate access by one or more instruments. One or more additional expansion devices 300 may be deployed within the body lumen distally and/or proximally of the target tissue 322.

In various embodiments, one or more apertures 308 of a device 300 may be used as attachment points for other devices. For example, an aperture may accept a portion of a suture such that another portion of the suture may be coupled to a target tissue. The suture may have a length adjusted between the aperture and the target tissue to adjust a tension applied to the target tissue. A suture may be coupled to a surrounding target tissue. A suture may be preloaded to a device prior to insertion into a patient.

In various embodiments, an access area beneath and about a layer of target tissue may be visualized. Visualization may be optical, fluoroscopic, ultrasonic, etc. The visualization of the area beneath and about the layer of target tissue may not be adequately revealed for the medical professional to manipulate a medical device to or near the layer of target tissue. The medical professional may deliver and deploy a tissue tensioning device or system to the layer of target tissue with a tension that reveals the access area for the procedure. The medical professional may adjust the length or tension of the system based on visualization of the layer of target tissue or nearby area.

In various embodiments, a suture may be engaged with a variety of different fasteners configured to engage the suture along with a tissue, such as a clip, an anchor, a screw, a pin, or the like. For example, a fastener contemplated for use with a suture may include a biased-open configuration configured to move to a closed/clamped configuration upon actuation by a handle assembly. In addition, or alternatively, a tissue fastener may include a biased-closed configuration configured to move an open configuration upon actuation of a distal end effector (e.g., squeezing) by a proximal handle assembly. In addition, or alternatively, fasteners other than detachable/releasable tissue fasteners may be used to secure/engage a suture to the wall of a body lumen, such as non-repositionable fasteners.

In various embodiments described herein, a method for forming a scaffold within a body lumen may include delivering a plurality of segments disposed along a filament to a working volume of the body lumen. The plurality of segments may have a delivery configuration. The filament may be proximally translated with respect to the plurality of segments to cause each of the plurality of segments to abut an adjacent other one of the plurality of segments to form a tensioned configuration having an outer dimension that is larger than an outer dimension of the delivery configuration. The plurality of segments may be maintained in the tensioned configuration by tension in the filament caused by the proximal translation. An open space between the plurality of segments in the tensioned configuration may be aligned towards a working volume of the body lumen. Proximally translating the filament may include translating the filament with respect to a stop member disposed about the filament proximal to the plurality of segments. The tension of the filament may be released such that the plurality of segments transitions from the tensioned configuration to the delivery configuration. A first end of a tissue traction device may be coupled to a segment of the plurality of segments. A second end of the tissue traction device may be coupled to a target tissue, thereby applying tension to the target tissue.

In various embodiments described herein, a method for forming a scaffold within a body lumen may include delivering a device comprising a tubular base having a plurality of self-expanding leaves extending from the tubular base to a working volume of the body lumen. The device may have a delivery configuration with the plurality of self-expanding leaves oriented substantially parallel with a longitudinal axis of the device. A sheath disposed about the device may be proximally translated to transition the device from the delivery configuration to a deployed configuration wherein a distal end of each of the plurality of self-expanding leaves extends radially away from the longitudinal axis. A suture coupled to a leaf of the plurality of leaves may be extended to a target tissue to apply tension to the target tissue. The device may be deployed into the body lumen from about an endoscope. The device may be retrieved by extending an endoscope through the lumen of the device and extending the sheath about the plurality of leaves thereby transitioning the device from the deployed configuration to the delivery configuration.

In various embodiments described herein, a method of applying tension to a tissue may include coupling a suture to an aperture of a device. A tissue-engaging portion of the suture may engage a layer of target tissue. The suture may be moved, adjusting a tensional force along the suture and applied to the layer of target tissue for retraction. A clamping device may be delivered about the layer of target tissue and clamp the layer of target tissue.

All of the devices and/or methods disclosed and claimed herein can be made and executed without undue experimentation in light of the present disclosure. While the devices and methods of this disclosure have been described in terms of preferred embodiments, it may be apparent to those of skill in the art that variations can be applied to the devices and/or methods and in the steps or in the sequence of steps of the method described herein without departing from the concept, spirit and scope of the disclosure. All such similar substitutes and modifications apparent to those skilled in the art are deemed to be within the spirit, scope and concept of the disclosure as defined by the appended claims.

What is claimed is:

1. An expandable device for a body lumen, comprising:
  a filament comprising a proximal end, a distal end, and a length; and
  a plurality of segments, each segment comprising:
    a middle portion comprising a longitudinal axis extending axially therethrough;

a projection portion extending from an end of the middle portion along the longitudinal axis;

a receptive portion extending from an opposing end of the middle portion, the receptive portion extending in a direction away from the longitudinal axis, the receptive portion configured to receive the projection portion of an adjacent one of the plurality of segments; and an aperture disposed through the projection portion, the middle portion, and the receptive portion, wherein the filament extends through the aperture;

wherein the device is shiftable between a generally elongated delivery configuration, and a tensioned configuration having a generally helical configuration for holding open the body lumen.

2. The expandable device of claim 1, wherein the plurality of segments abut adjacent segments of the plurality of segments along the filament to form an expanded helical shape in the tensioned configuration.

3. The expandable device of claim 2, wherein the tensioned configuration is achieved by proximally translating the filament with respect to a stop member disposed about the filament to thereby press each of the plurality of segments against adjacent ones of the plurality of segments.

4. The expandable device of claim 2, wherein the expanded shape comprises a helix having a first space between first and second windings and a second space between third and fourth windings larger than the first portion.

5. The expandable device of claim 1, wherein:
the projection portion tapers away from the middle portion to a tip having a smaller dimension than a dimension of the middle portion; and
the receptive portion comprises a cavity defining a volume that compliments a shape of the projection portion.

6. The expandable device of claim 5, wherein the tip of the projection portion terminates at a first planar surface transverse with a centerline extending through the segment.

7. The expandable device of claim 6, wherein the cavity of the receptive portion terminates at a second planar surface transverse with the centerline.

8. The expandable device of claim 7, further comprising:
a first axis extending along the first planar surface at the largest dimension of the first planar surface; and
a second axis extending along the second planar surface at the largest dimension of the second planar surface, wherein the second axis is angled obliquely apart from the first axis.

9. The expandable device of claim 5, wherein the tip of the projection portion comprises a first planar surface transverse with the longitudinal axis and a remainder of the projection portion comprises two slanted planes disposed 180 degrees apart when viewed along the longitudinal axis and two convex surfaces disposed 180 degrees apart when viewed along the longitudinal axis.

10. The expandable device of claim 1, further comprising an end portion disposed at the distal end of the filament, the end portion comprising a larger dimension than a dimension of the aperture of each of the plurality of segments.

11. The expandable device of claim 1, wherein the filament engages at least one of said plurality of segments in the tensioned configuration.

12. The expandable device of claim 1, wherein the distal end of the filament is adhered to a distal-most segment of the plurality of segments.

13. The expandable device of claim 1, wherein the device comprises an arc shape in the tensioned configuration.

14. The expandable device of claim 1, further comprising a suture coupled to an aperture of at least one of the plurality of segments.

15. The expandable device of claim 1, wherein the first outer dimension is at most about 4.2 mm and wherein the second outer dimension is at least 18 mm.

16. An expandable system for a body lumen, comprising:
an expandable device comprising:
a tubular base having a proximal end and a distal end, and defining a lumen therethrough along a longitudinal axis; and
a plurality of self-expanding leaves extending from the distal end of the tubular base, each of the plurality of self-expanding leaves having proximal and distal ends, the proximal ends associated with the distal end of the tubular base, the plurality of self-expanding leaves oriented substantially parallel with the longitudinal axis in a delivery configuration, the distal ends of the plurality of self-expanding leaves extending radially away from and spaced away from the longitudinal axis of the tubular base in a deployed configuration; and
a sheath slidably extendable about the tubular base and the plurality of self-expanding leaves to move the plurality of self-expanding leaves between the delivery configuration and the deployed configuration and to deploy the tubular base;
wherein proximal movement of the sheath relative to the expandable device separates and deploys the expandable device from the sheath with the proximal end of the tubular base deployed outside the sheath and the plurality of self-expanding leaves extending radially away from the tubular base.

17. The expandable system of claim 16, wherein the distal end of each of the plurality of self-expanding leaves is configured to curl outwardly away from the lumen in the deployed configuration.

18. The expandable system of claim 16, wherein each of the plurality of self-expanding leaves comprises an end configured to curl toward a proximal end of the longitudinal axis in the deployed configuration.

19. The expandable system of claim 16, wherein the distal end of each of the at least one of the plurality of self-expanding leaves comprises an aperture configured to receive a suture, the suture having a tissue-engaging portion for engaging tissue and for applying tension to the tissue via the associated self-expanding leaf.

20. The expandable system of claim 16, further comprising a catheter extending through the lumen.

* * * * *